United States Patent
Bertin et al.

(10) Patent No.: US 8,922,641 B2
(45) Date of Patent: Dec. 30, 2014

(54) SYSTEM AND METHOD FOR INSPECTING COMPONENTS OF HYGIENIC ARTICLES

(75) Inventors: Jeremy Georges Bertin, Plainfield (CA); Rajesh Kumar Singh, Deerfield, OH (US); Markus Ingo Hoffmann, Marktlustenau (DE); Randolph William Lumsden, Belleville (CA)

(73) Assignee: The Procter & Gamble Company, Cincinnati, OH (US)

( * ) Notice: Subject to any disclaimer, the term of this patent is extended or adjusted under 35 U.S.C. 154(b) by 560 days.

(21) Appl. No.: 13/172,463

(22) Filed: Jun. 29, 2011

(65) Prior Publication Data

US 2013/0002852 A1 Jan. 3, 2013

(51) Int. Cl.
*H04N 9/47* (2006.01)
*H04N 7/18* (2006.01)
*G06T 7/00* (2006.01)
*G01N 21/956* (2006.01)

(52) U.S. Cl.
CPC .......... *G06T 7/001* (2013.01); *G01N 21/95607* (2013.01); *G06T 2207/30124* (2013.01); *G06T 2207/30144* (2013.01)
USPC ................. 348/92; 348/86; 348/88; 348/135

(58) Field of Classification Search
None
See application file for complete search history.

(56) References Cited

U.S. PATENT DOCUMENTS

| | | | |
|---|---|---|---|
| 5,187,376 A | 2/1993 | Hashimoto et al. | |
| 5,237,181 A | 8/1993 | Kerkhoff et al. | |
| 5,305,392 A | 4/1994 | Longest, Jr. et al. | |
| 5,365,084 A | 11/1994 | Cochran et al. | |
| 5,365,596 A | 11/1994 | Dante et al. | |
| 5,374,988 A | 12/1994 | Wertz et al. | |
| 5,426,509 A | 6/1995 | Peplinski | |
| 5,439,558 A | 8/1995 | Bergmann et al. | |
| 5,440,648 A | 8/1995 | Roberts et al. | |
| 5,570,633 A | 11/1996 | Schultz et al. | |
| 5,640,200 A | 6/1997 | Michael | |
| 5,673,334 A | 9/1997 | Nichani et al. | |
| 5,712,921 A | 1/1998 | Zabele | |
| 5,724,437 A | 3/1998 | Bucher et al. | |
| 5,732,529 A | 3/1998 | Dey et al. | |
| 5,735,785 A | 4/1998 | Lucas et al. | |
| 5,776,297 A | 7/1998 | Edwards et al. | |
| 5,792,296 A | 8/1998 | Soltysiak | |
| 5,838,840 A | 11/1998 | King et al. | |
| 5,880,772 A | 3/1999 | Kalnajs et al. | |
| 5,912,984 A | 6/1999 | Michael et al. | |
| 5,949,901 A | 9/1999 | Nichani et al. | |
| 5,990,468 A | 11/1999 | Cornuejois | |
| 5,999,636 A | 12/1999 | Juang | |
| 6,026,172 A | 2/2000 | Lewis, Jr. et al. | |
| 6,061,476 A | 5/2000 | Nichani | |
| 6,112,658 A | 9/2000 | Gunther et al. | |
| 6,119,594 A | 9/2000 | Kipphan et al. | |
| 6,148,724 A | 11/2000 | Hart et al. | |
| 6,166,366 A | 12/2000 | Lewis et al. | |
| 6,170,747 B1 | 1/2001 | Meyer | |

(Continued)

*Primary Examiner* — Joseph Ustaris
*Assistant Examiner* — Kevin McInnish
(74) *Attorney, Agent, or Firm* — George H. Leal; Megan C. Hymore

(57) ABSTRACT

System and method to inspect hygienic articles. Defects are detected using a vision system by comparing an inspection image of a component to a reference image of a defect-free component. Detection of a defect can then be used to reject components and perform other functions.

16 Claims, 5 Drawing Sheets
(1 of 5 Drawing Sheet(s) Filed in Color)

(56) References Cited

U.S. PATENT DOCUMENTS

| | | |
|---|---|---|
| 6,236,747 B1 | 5/2001 | King et al. |
| 6,259,109 B1 | 7/2001 | Dalmia et al. |
| 6,269,194 B1 | 7/2001 | Nichani |
| 6,294,111 B1 | 9/2001 | Shacklett, III et al. |
| 6,295,374 B1 | 9/2001 | Robinson et al. |
| 6,324,353 B1 | 11/2001 | Laussermair et al. |
| 6,456,733 B1 | 9/2002 | Miyauchi et al. |
| 6,608,697 B1 | 8/2003 | Schorr et al. |
| 6,721,461 B1 | 4/2004 | Nichani |
| 6,746,164 B1 | 6/2004 | Albright et al. |
| 6,750,466 B2 | 6/2004 | Guha et al. |
| 6,796,240 B2 | 9/2004 | Sainio et al. |
| 6,811,239 B1 | 11/2004 | Salacz |
| 6,829,516 B2 | 12/2004 | Popp et al. |
| 6,874,420 B2 | 4/2005 | Lewis, Jr. et al. |
| 6,880,952 B2 | 4/2005 | Kiraly et al. |
| 6,909,502 B2 | 6/2005 | Capaldo et al. |
| 6,928,182 B1 | 8/2005 | Chui |
| 7,123,981 B2 | 10/2006 | Dollevoet et al. |
| 7,203,340 B2 | 4/2007 | Gorodnichy |
| 7,260,244 B2 | 8/2007 | Shikami et al. |
| 7,408,570 B2 | 8/2008 | Guha et al. |
| 7,423,280 B2 | 9/2008 | Pearson et al. |
| 7,570,796 B2 | 8/2009 | Zafar et al. |
| 7,635,087 B1 | 12/2009 | Chung et al. |
| 7,693,432 B2 | 4/2010 | Belinkov et al. |
| 7,731,331 B2 | 6/2010 | Karrer et al. |
| 7,813,827 B2 | 10/2010 | Key |
| 2004/0022426 A1* | 2/2004 | Carbone et al. ............... 382/141 |
| 2005/0154485 A1* | 7/2005 | Popp et al. ................... 700/124 |

* cited by examiner

US 8,922,641 B2

SYSTEM AND METHOD FOR INSPECTING COMPONENTS OF HYGIENIC ARTICLES

FIELD OF THE INVENTION

The present invention relates generally to a system and method for inspecting components of hygienic articles. More particularly, defects are detected by comparing an inspection image of a component to a reference image of a defect-free component.

BACKGROUND OF THE INVENTION

Hygienic articles, such as feminine hygiene products (e.g., pantiliners or pads), disposable diapers, pull-ons, training pants, and adult incontinence articles, often include features such as printed images and printed text. Such features are often used for both functional and aesthetic reasons. For example, a diaper may include a popular design (e.g., a popular children's character, a team logo, and other familiar designs), to increase consumer awareness of the product.

Generally, consumers expect each hygienic article to maintain the same look and feel as one another. In most cases, hygienic articles are used sequentially by a consumer from a package, meaning that the consumer is able to more readily distinguish differences between the individual articles and notice any defects that may be present. For example, the placement of a popular design on a diaper must be consistently placed, in order to ensure that the design is fully shown (e.g., that a headless character is not shown, a team logo is not missing the name of the team's city, and other inconsistencies). These types of defects may be caused by a number of different problems in the manufacturing process. For example, a feature may be improperly placed onto a component, if the component is not positioned correctly. In another example, a printer requiring maintenance may smear a feature as it is printed onto a component.

In certain cases, it may even be desirable for hygienic articles within a package to be different. For example, a manufacturer may wish to ensure that each hygienic article in a package has a separate design. In another example, the manufacturer may wish to ensure that the package contains only a certain number of articles having the same design. In such cases, the manufacturer must ensure that each hygienic article is free from defects, as well as impose any additional limitations on how the articles are packaged.

Quality inspection of components by the naked eye is often time consuming and prone to human error. Therefore, recent efforts have been made in the field of manufacturing hygienic articles to automate some or all of the manufacturing process. However, it remains challenging and difficult to develop new techniques and systems that automatically inspect components of hygienic articles to ensure quality and consistency.

SUMMARY OF THE PRESENT INVENTION

The present invention relates to a method of inspecting a component of a hygienic article comprising: storing, within a memory, a reference image of a first component used to produce a hygienic article, wherein the first component is free of defects and comprises a feature and wherein the reference image is captured when the first component passes a camera; illuminating, at the camera, a second component with a color that increases the contrast of a feature of the second component within an image; triggering, by a trigger device, the capture of an inspection image of the second component by the camera; generating, by a processor, a residual image by performing image subtraction between the reference image and the inspection image; detecting, by the processor, a variation between the first component and the second component using the residual image; and generating a rejection command that causes the second component to be rejected, in response to the variation being detected.

The present invention further relates to an inspection system for the manufacture of hygienic articles comprising: a camera; one or more lights that illuminate hygienic article components, wherein each component has a feature, and wherein each component is illuminated with a color that increases the contrast of the feature within an image; and a controller comprising one or more processors and one or more non-transitory memory devices communicatively coupled to the one or more processors, wherein the one or more memory devices store machine instructions that, when executed by the one or more processors, cause the one or more processors to: generate a first image capture command that causes the camera to capture a reference image of a first hygienic article component, wherein the first component is free of defects; generate a second image capture command that causes the camera to capture an inspection image of a second hygienic article component, in response to receiving a trigger command from a trigger device; generate a residual image by performing image subtraction using the reference image and the inspection image; detect a variation between the first component and the second component using the residual image; and generate a rejection command that causes the second component to be rejected, in response to the variation being detected.

The present invention still further relates to an inspection system for the manufacture of hygienic articles comprising: a camera; one or more processors; and one or more non-transitory memory devices communicatively coupled to the one or more processors, wherein the one or more memory devices store machine instructions that, when executed by the one or more processors, cause the one or more processors to: generate a first image capture command that causes the camera to capture a reference image of a first hygienic article component, wherein the first component is free of defects; generate a second image capture command that causes the camera to capture an inspection image of a second hygienic article component, in response to receiving a trigger command from a trigger device; generate a residual image by performing image subtraction using the reference image and the inspection image; detect a variation between the first component and the second component using the residual image; and generate a rejection command that causes the second component to be rejected, in response to the variation being detected.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of the present disclosure can be best understood when read in conjunction with the following drawings, where like structure is indicated with like reference numerals and in which.

Figure 1:
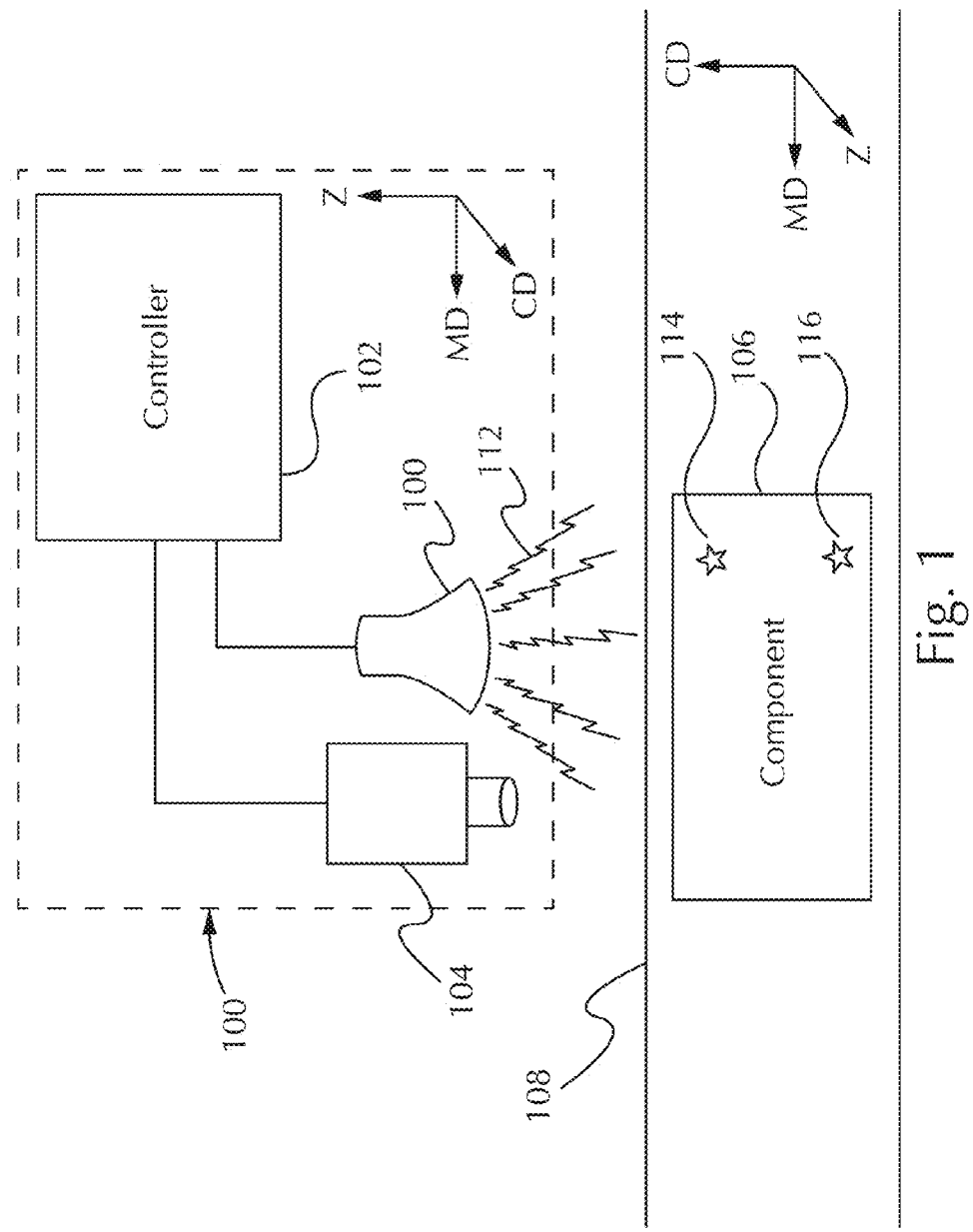
FIG. 1 is a schematic illustration of a vision system.

Individual aspects of the drawings will be more fully apparent and understood in view of the detailed description that follows.

DETAILED DESCRIPTION

Present techniques to help automate the manufacture of hygienic articles often fail to inspect components for quality and consistency, require the use of timing marks on the product itself, and/or require making considerable manual adjustments to the manufacturing process. It has been discovered that utilizing a vision system to inspect component features for quality and consistency further automates the manufacturing process and helps to reduce the effects of human error in the process.

As used herein, the following terms are defined as follows:

"Hygienic article" and "disposable absorbent article" refer to feminine hygiene products (e.g., pantiliners or pads), disposable diapers, pull-ons, training pants, and adult incontinence articles. Examples of goods that are not hygienic articles or disposable absorbent articles for purposes of this disclosure include paper towels, toilet paper, facial tissues, newspaper, magazines, and books.

"Disposable" refers to products which are not intended to be laundered or otherwise restored or extensively reused in their original function, i.e., preferably they are intended to be discarded after several uses or after a single use.

"Machine direction" (MD) refers to the direction of movement of a component along a manufacturing line.

"Cross direction" (CD) refers to the direction substantially perpendicular or perpendicular to the MD and across the component as it moves along a manufacturing line.

"Component" refers to any material, part, or combination of materials and/or parts used in the construction of a final good by a manufacturing system.

"Feature" refers to any surface area of a component that provides an optical contrast with another area of the component. In non-limiting examples, a feature may be a graphic or text that is printed, dyed, painted, or otherwise applied to a component. In some cases, the graphic may simply be a coloration of a portion of the component (e.g., a peanut-shaped core), a pattern (e.g., flowers, hearts, stars, swirls, and combinations thereof), a simple design (e.g., a symbol or shape), or a more complicated design (e.g., a logo, an image, a children's character, a scenic print, a brand name, a trademark, or the like), and combinations thereof. For purposes of this specification, apertures and holes are explicitly excluded from the definition of a feature.

"Color" refers to the spectral properties of light that can be perceived and distinguished by the naked eye or by an optical sensor. Non-limiting examples of color include infrared, red, orange, yellow, green, blue, indigo, violet, ultraviolet, as well as any declination or mixture thereof. For purposes of this application, black, white, and gray are explicitly excluded from this definition. For example, although white light may include wavelengths that may be categorized as red, it is perceived as being white and is, therefore, neither red nor colored light for purposes of this application.

"Grayscale" refers to the representation of an image using only black, white, and/or shades of gray.

"Controller" refers to any electronic device or system that provides control commands to another electronic and/or mechanical system. A controller includes one or more processors (e.g., a microprocessor, central processing unit, application-specific integrated circuit, or the like). A controller may also include one or more memory devices (e.g., a RAM, ROM, non-volatile memory, flash memory, non-transitory memory, hard drive, disk drive, or any other electronic device capable of storing machine instructions) that communicate locally or remotely with the one or more processors. The one or more memory devices store machine instructions that, when executed by the one or more processors, cause the one or more processors to provide the control commands. Non-limiting examples of controllers include personal computers, servers, programmable logic controllers (PLCs), tablet computers, handheld computing devices, mobile telephones, distributed computing systems, cameras, and electronic displays.

In general, a vision system includes one or more cameras that capture images of components as they move through the manufacturing process. Any known type of electronic camera may be used. For example, a camera may be a charge-coupled device, a CMOS-pixel based device, a combination of the two, or any other electronic device that converts received photons into data. Additionally, a camera may capture images in grayscale, in color, or both. The image data captured by a camera is provided to one or more controllers for further analysis. A camera may also have one or more controllers integrated as part of the device (e.g., within the same housing as the camera) and/or transmit the image data to one or more controllers external to the camera. The one or more controllers analyze the image data to ensure that a feature of the component meets the manufacturer's standards for quality and consistency. If the feature is not present, misaligned, or containing errors (e.g., is incorrectly sized, is too dark or light, utilizes the wrong color, is smeared, or the like), the one or more controllers may generate control signals that cause the component to be rejected. In some cases, the one or more controllers may also adjust an upstream device that placed the feature on the component and/or alert a human operator that maintenance may be necessary.

A method of inspecting a component of a hygienic article is shown and described herein. The method includes storing, within a memory, a reference image of a first component used to produce a hygienic article, wherein the first component is free of defects and wherein the reference image is captured when the first component passes a camera. The method also includes illuminating, at the camera, a second component, wherein the illumination color increases the contrast of a feature of the second component within an image. The method further includes triggering, by a trigger device, the capture of an inspection image of the second component by the camera and generating, by a processor, a residual image by performing image subtraction between the reference image and the inspection image. The method yet further includes detecting, by the processor, a variation between the first component and the second component using the residual image and generating a rejection command that causes the second component to be rejected, in response to the variation being detected.

An inspection system for the manufacture of hygienic articles is shown and described herein. The inspection system includes a camera, one or more lights that illuminate hygienic article components, and a controller. Each component has a feature and is illuminated with a color that increases the contrast of the feature within an image. The controller includes one or more processors and one or more non-transitory memory devices communicatively coupled to the one or more processors. The one or more memory devices store machine instructions that, when executed by the one or more processors, cause the one or more processors to generate a first image capture command that causes the camera to capture a reference image of a first hygienic article component that is free of defects. The instructions further cause the one or more processors to generate a second image capture command that causes the camera to capture an inspection image of a second hygienic article component, in response to receiving a trigger command from a trigger device, and to generate a residual image by performing image subtraction using the reference image and the inspection image. The instructions yet further cause the one or more processors to detect a variation between the first component and the second component using the residual image and to generate a rejection command that causes the second component to be rejected, in response to the variation being detected.

An inspection system for the manufacture of hygienic articles is shown and described herein. The inspection system includes a camera, one or more processors, and one or more non-transitory memory devices communicatively coupled to the one or more processors. The one or more memory devices store machine instructions that, when executed by the one or more processors, cause the one or more processors to generate a first image capture command that causes the camera to capture a reference image of a first hygienic article component that is free of defects. The instructions further cause the one or more processors to generate a second image capture command that causes the camera to capture an inspection image of a second hygienic article component, in response to receiving a trigger command from a trigger device, and to generate a residual image by performing image subtraction using the reference image and the inspection image. The instructions yet further cause the one or more processors to detect a variation between the first component and the second component using the residual image, and to generate a rejection command that causes the second component to be rejected, in response to the variation being detected.

Referring now to FIG. 1, an illustrative schematic of vision system 100 is shown. Vision system 100 includes camera 104. As shown, camera 104 may be positioned in a fixed location and capture an electronic image of a component 106, as it passes vision system 100 in the machine direction along manufacturing line 108. Camera 104 may be oriented in any number of positions in relation to the direction of motion of component 106. For example, camera 104 may be positioned above or below component 106, along the side of component 106, or somewhere therebetween. In some cases, camera 104 may be able to take continuous images (e.g., video). In other cases, camera 104 may only be able to capture still-frame images. If video is used, still-frame images may be discerned by analyzing the video at discrete times. If camera 104 captures still-frame images outright, it may do so periodically or in response to receiving a trigger command from an upstream and/or downstream trigger device that senses when components pass the trigger device.

Camera 104 provides a captured electronic image to controller 102, which analyzes the image to ensure that feature 114 of component 106 meets the manufacturer's standards for quality and consistency. If feature 114 is missing or does not conform to the predefined standards, controller 102 may generate a rejection command that causes a downstream device to remove the rejected component 106 from manufacturing line 108. Controller 104 may additionally or alternatively generate an alert to an interface device (e.g., a display, a speaker, or the like) that alerts a human operator about the rejection. In this way, vision system 100 is able to cull defective components from being used in finalized hygienic articles.

In some cases, controller 102 may also maintain a history of rejections and use the history of rejections to initiate corrective measures in the upstream device that produced the feature. For example, feature 114 may be printed onto component 106 by an upstream inkjet printer, such as the one disclosed in U.S. Pat. No. 6,811,239 to Salacz, which is commonly assigned and hereby incorporated by reference. As the printer is used, its active print head may malfunction or require cleaning, causing feature 114 to smear or otherwise be unacceptable. If controller 102 determines that the number of rejections exceeds a threshold, controller 102 may generate a switching command that causes the printer to switch print heads.

If camera 104 captures images in grayscale, vision system 100 may also include lighting 110. Lighting 110 includes one or more light sources (e.g., an incandescent bulb, halogen lamp, light emitting diode, or any other device that emits photons). In some cases, some or all of the light sources of lighting 110 may be controlled by controller 102 (e.g., turned on when component 106 passes vision system 100). In other cases, some or all of the light sources of lighting 110 may be on continuously.

Currently, cameras that capture images in grayscale provide a cheaper alternative to cameras that do so in color. However, grayscale images are often more difficult to analyze than color images, since color provides a useful mechanism by which to identify a feature on a component. If grayscale images are used in vision system 100, the one or more light sources of lighting 110 may emit colored light 112 that increases the contrast of feature 114 in a grayscale image captured by camera 104. For example, if feature 114 is printed onto component 106 using blue ink, illuminating it with red light would maximize the contrast of feature 114 in the captured grayscale image.

In some cases, component 106 may also include feature 116, which is of a different color than that of feature 114. In such a case, lighting 110 may also include light sources that emit colors that further maximize the contrast of feature 116 in the captured grayscale image. For example, if feature 116 is printed onto component 106 using pink ink, illuminating it with green light would maximize the contrast of feature 116 in the capture grayscale image.

Component 106 may include any number of features of varying colors and that lighting 110 can be adapted accordingly to maximize the contrast of each of these features. In one case, each feature may be illuminated separately by its corresponding color to maximize its contrast, either sequentially or in unison. In this case, one or more cameras may be utilized to capture one or more images for analysis. For example vision system 100 may include multiple grayscale cameras that capture images of particular sets of colors. In another case, if the component includes multiple features of varying colors, lighting 110 can be adapted to utilize a color that is an average of the colors that would maximize the contrast of these features.

Figure 2:
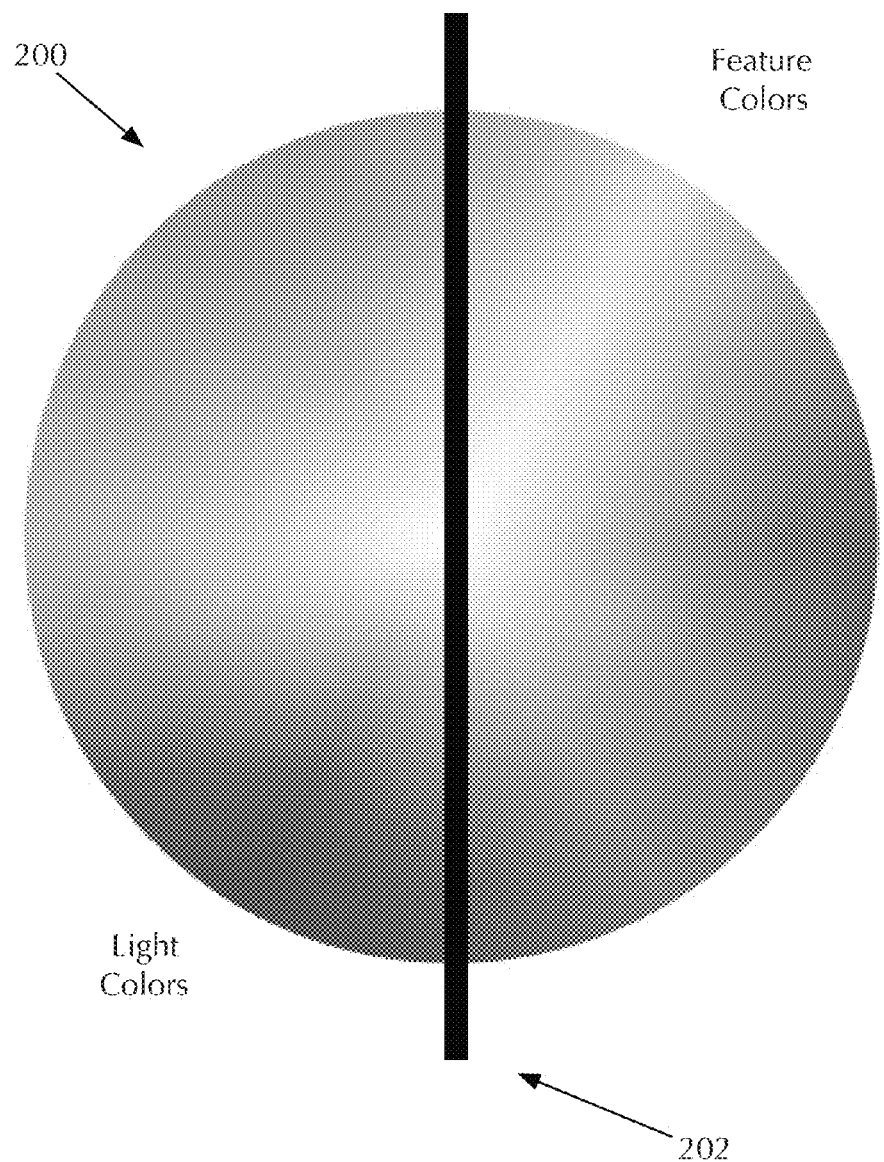
FIG. 2 is an illustration of a color spectrum.

Referring now to FIG. 2, an illustration of a color spectrum is shown. Color spectrum 200 may be used to select a color of lighting that increases the contrast of a component feature in a grayscale image. As shown, line 202 divides color spectrum 200 into a category of colors that may be used for lighting and a category of colors that may be used for the component features. It is to be appreciated that line 202 is exemplary only and that line 202 may be rotated about the center of color spectrum 200 to define any number of categories of lighting and feature colors.

Opposing colors in color spectrum 200 (e.g., colors that are approximately 180° from each other in FIG. 2) provide the highest amount of contrast in a grayscale image, allowing a color of light to be selected based on the color of the feature. For example, if a feature is pink, illuminating it with green light maximizes the contrast of the feature in a grayscale image. In another example, illuminating a blue feature with red light would also maximize the contrast of that feature. In a further example, illuminating a purple feature with yellow light maximizes the contrast of that feature. In this way, any number of colors for the lighting in a vision system can be selected.

In some cases, an average of colors may be used to increase the contrast of two or more features. For example, if a component contains both purple and light blue features, their optimal illumination colors would be green and red, respectively. However, yellow light may be used instead to increase the contrast of both of the features, since yellow is the average color between green and red.

Figure 3A:
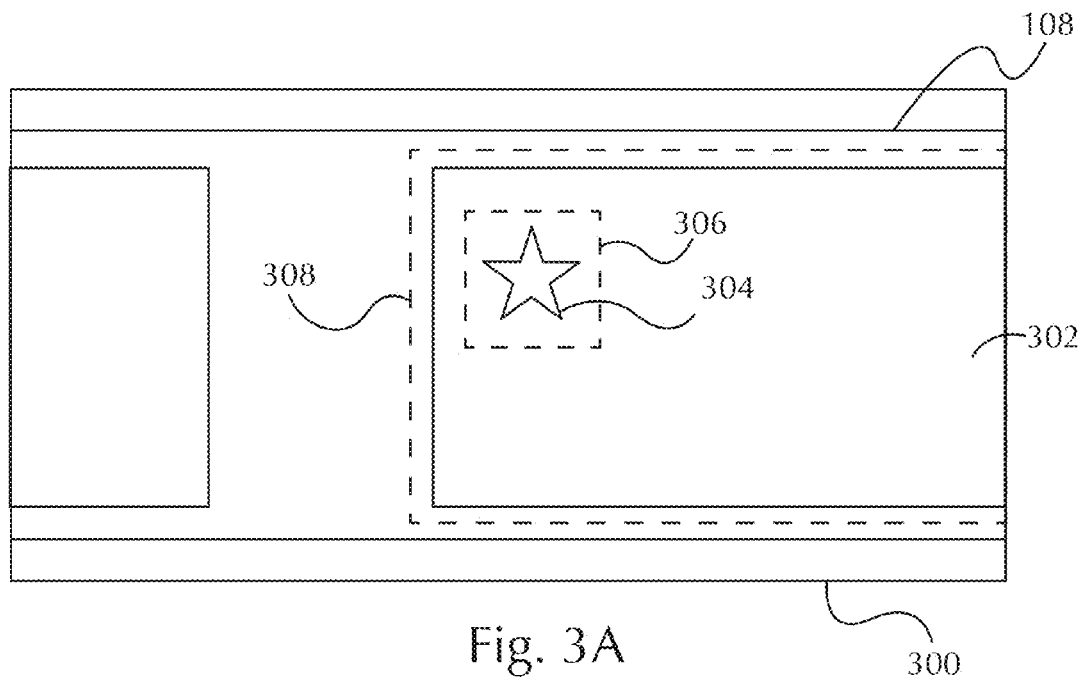
FIG. 3A is an illustration of a reference image.

Referring now to FIG. 3A, an illustration of a reference image 300 is shown. Reference image 300 is captured by vision system 100, as a component 302 travels along manufacturing line 108. Component 302 is used to produce a finalized hygienic article and is free from defects. Component 302 includes a feature 304, which is placed onto component 302 by an upstream device. If reference image 300 is a grayscale image, lighting 110 of vision system 100 may be color matched to the color of feature 304, in order to produce the maximum contrast in image 300.

In some cases, an operator (e.g., utilizing an interface device of controller 102) may specify one or more subsets of reference image 300, indicated by dashed lines. The one or more subsets are then used by controller 102 to analyze subsequent images. For example, subset 308 may be used to analyze all of component 302 shown in reference image 300. In another example, subset 306 may be used to analyze only the area of reference image 300 immediately surrounding feature 304. As can be appreciated, any number of subsets having any number of different shapes and sizes may be used by vision system 100.

Figure 3B:
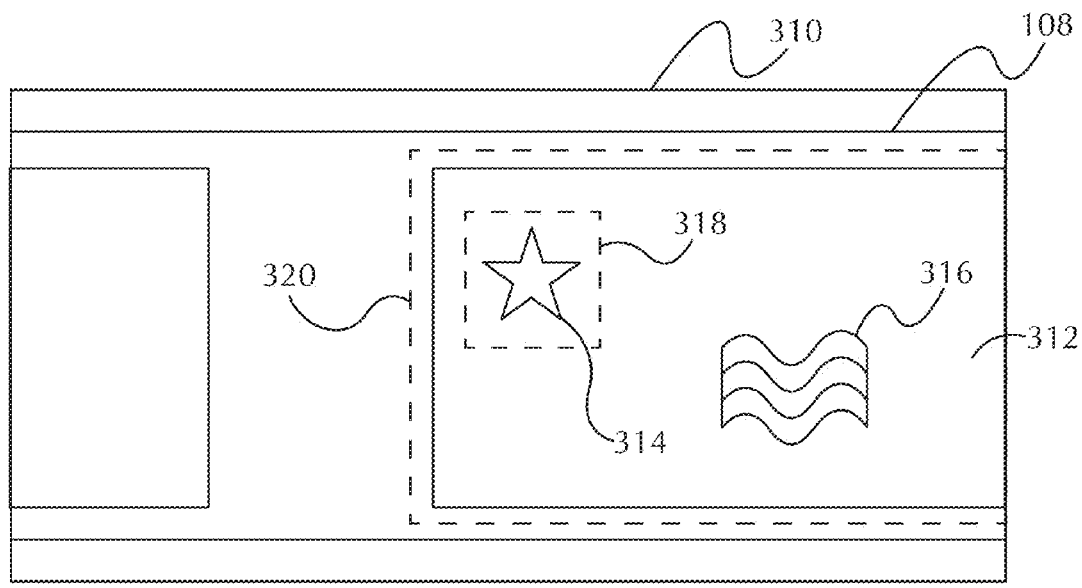
FIG. 3B is an illustration of an inspection image.

Referring now to FIG. 3B, an illustration of an inspection image 310 is shown. Similar to reference image 300, inspection image 310 is captured by vision system 100 as a component 312 travels along manufacturing line 108. Component 302 also contains a feature 314, which corresponds to feature 304 of component 302. Unlike component 302 however, component 312 also contains defect 316. Controller 102 analyzes inspection image 310 to detect variations between reference image 300 and inspection image 310, such as defect 316.

In some cases, controller 102 uses the regions defined by the one or more specified subsets of reference image 300 as part of the inspection of component 312. For example, the region defined by subset 306 of reference image 300 may be used to define a corresponding subset 318 in inspection image 310. Similarly, the region defined by subset 308 can be used to define a corresponding subset 320 in inspection image 310. In this way, different subsets can be used by controller 102 to analyze inspection image 310.

Image subtraction provides one way to compare inspection image 310 to reference image 300. Using such a technique, controller 102 determines the difference between inspection image 310 and reference image 300 or between a subset of reference image 300 and a corresponding subset of inspection image 310 (e.g., between subsets 306 and 318, between subsets 308 and 320, or the like). In this way, variations such as defect 316 can be detected by controller 102.

Figure 3C:
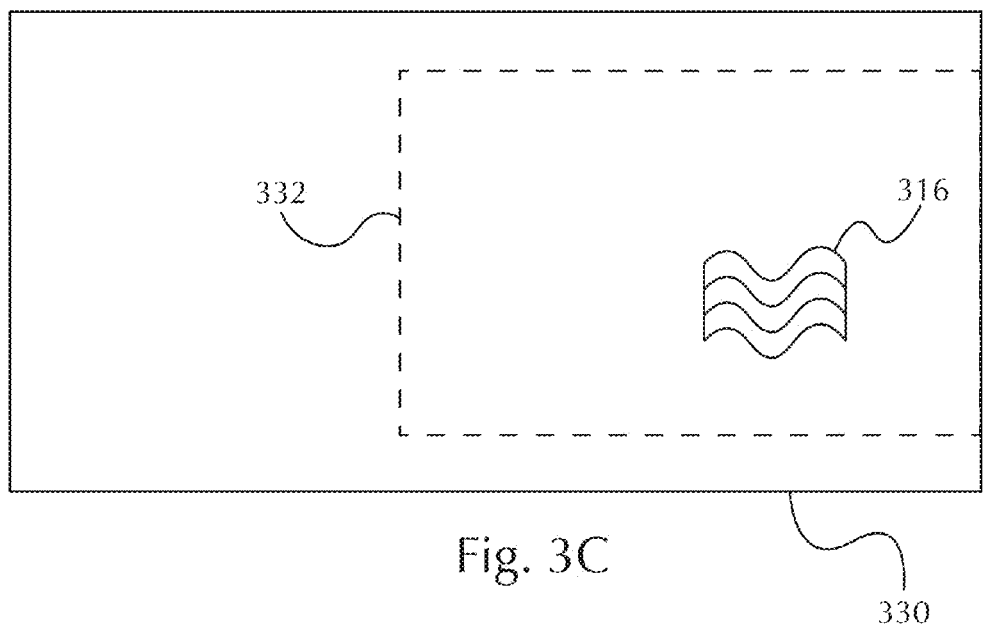
FIG. 3C is an illustration of a residual image.

Referring now to FIG. 3C, an illustration of a residual image 330 is shown. Residual image 330 is generated by finding the difference between subset 308 of reference image 300 and subset 320 of inspection image 310, i.e., a subset 332 of residual image 330. Residual image 330 is then analyzed for the presence of differences, such as defect 316, which exists on component 310, but not on component 302. If defect 316 is of a type that requires rejection of component 310, controller 102 may then generate a rejection command that causes a rejection device in the manufacturing system to remove component 310 from manufacturing line 108 and/or an alarm as set forth herein.

Performing image subtraction between some or all of a reference image and some or all of an inspection image allows the detection of misplaced features, missing features, the presence of additional defects (e.g., a feature that is discolored, improperly sized, improperly shaded, smeared, and the like), and/or desirable features (e.g., if a limit is imposed on how many hygienic articles having the same look may be placed in a single package). In certain cases, the controller analyzing the images may utilize one or more thresholds that specify when a rejection command and/or an alert should be generated. For example, a feature that is off center from its correct location, but is otherwise intact, may still be acceptable within a certain distance threshold. In such a case, the controller may only issue a rejection command and/or an alert if the distance to the correct location exceeds a specified threshold.

Figure 4:
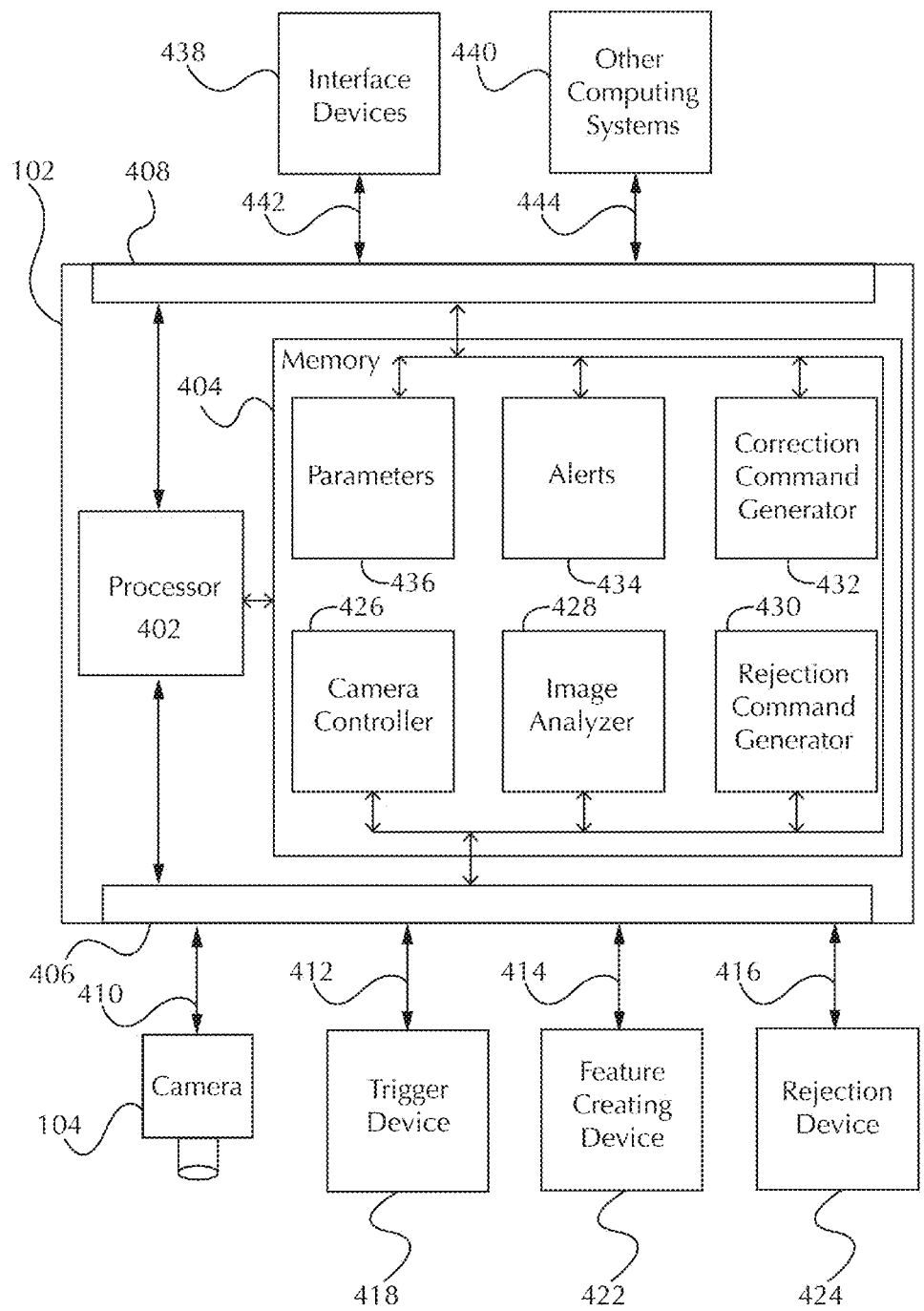
FIG. 4 is a schematic illustration of the controller shown in FIG. 1.

Referring now to FIG. 4, a schematic illustration of the manufacturing system and controller 102 is shown. Controller 102 includes a processor 402, which may be one or more processors communicatively coupled to a memory 404, interface 406, and interface 408. Memory 404 may be any form of memory capable of storing machine-executable instructions that implement one or more of the functions disclosed herein, when executed by processor 402. For example, memory 404 may be a RAM, ROM, flash memory, hard drive, EEPROM, CD-ROM, DVD, other forms of non-transitory memory devices, or the like. In some cases, memory 404 may be any combination of different memory devices.

While controller 102 is shown as a single device, it is to be understood that this is exemplary only and that controller 102 may include processing components that span multiple physical devices, without deviating from the scope of the present disclosure. For example, processor 402 may include a processor that is part of camera 104 and a processor that is part of a remote server (e.g., other computing systems 440). In another example, memory 404 may include a hard drive of a remote server (e.g., other computing systems 440) and a non-volatile memory of camera 104.

Connections 410, 412, 414, and 416 provide one or more wired or wireless connections between controller 102 and camera 104, trigger device 418, feature creating device 422, and rejection device 424, respectively. In some cases, connections 410, 412, 414, and 416 may be combined connections. For example, connection 410 and 416 may be part of a shared data bus or backplane. Connections 410, 412, 414, and 416 may also provide direct connections to controller 102 or indirect connections (e.g., via one or more intermediary connection devices, such as a router, other controller, or the like). For example, connection 416 may be an indirect connection over a local area network (LAN).

Interface 406 provides the one or more wired or wireless connections 410, 412, 414, and 416 for controller 102. For example, interface 406 may provide a wireless connection between controller 102 and feature creating device 422 and provide a hardwired connection to camera 104. Non-limiting examples of the types of interfaces provided by interface 406 include a radio frequency transceiver, a WiFi transceiver, a Cat 5 port, a telephone jack, a serial bus, an I/O module, a USB port, and the like.

Trigger device 418 may be one or more sensors that are upstream and/or downstream from camera 104 and sense the passing of components. For example, trigger device 418 may be a programmable limit switch, a motion sensor, another vision system, or any other device that discerns the presence and/or timing of components as they pass. Since an inspection image must be captured when the component is in the same position as that of the reference image, trigger device 418 may be used by controller 102 to control the timing of when camera 104 captures images of components. In such a case, trigger device 418 provides a trigger command to controller 102 whenever a component is detected by it.

Feature creating device 422 is a device upstream from camera 104 that places one or more features onto the component being inspected by vision system 100. In non-limiting examples, feature creating device 422 may be a printer, an etcher, a painter, a laser, or any other device that adds a feature to a component of a hygienic article. In some cases, controller 102 may detect component defects and cause feature creating device 422 to correct the source of the defects (e.g., by switching print heads or the like).

Rejection device 424 is a device downstream from camera 104 that reroutes defective components from the manufacturing line. If controller 102 determines that an inspected component is defective, it generates a rejection command that causes rejection device 424 to remove the defective component from being further processed to make a hygienic article. In this way, vision system 100 is able to automatically cull defective components from the manufacturing process.

Connections 442 and 444 also provide one or more wired or wireless connections between controller 102, interface devices 438, and other computing systems 440. Connections 442 and 444 may be individual connections, shared connections, direct connections, and/or indirect connections. For example, connection 444 may be an indirect connection that connects controller 102 to other computing systems 440 via the Internet.

Similar to interface 406, interface 408 provides the one or more wired or wireless connections 442 and 444 for controller 102. In some cases, interfaces 406 and 408 may also be combined. For example, connections 414 and 444 may both utilize a WiFi connection to a LAN. In such a case, interfaces 406 and 408 may be combined and include a single WiFi transceiver that provide connections 414 and 444.

Interface devices 438 are one or more electronic devices that receive and/or convey information between controller 102 and a human user. In non-limiting examples, interface devices 438 may be one or more electronic displays, speakers, printers, portable electronic devices, keyboards, touch-screen displays, pointing devices, and the like. For example, an operator may utilize interface devices 438 to learn about the rejection of components by vision system 100 or to configure controller 102.

Other computing systems 440 are one or more computing devices (e.g., servers, personal computers, laptops, portable electronic devices, programmable logic controllers, and the like) that provide additional functionality to the manufacturing process. For example, other computing systems 440 may include a server that uses information about component rejections from controller 102 to generate reports about the rejected components.

Memory 404 includes camera controller 426 which generates image capture commands that cause camera 104 to capture images of components, as they pass camera 104. In some cases, camera controller 426 may receive a trigger command from trigger device 418 and use the trigger command to control the timing of when camera 104 captures an image. In other cases, trigger device 418 is omitted and camera controller 426 utilizes a timing value (e.g., stored in parameters 436) to determine when camera 104 captures images.

Image analyzer 428 receives the captured images from camera 104 and analyzes them. In some cases, image analyzer 428 stores one or more reference images of a defect-free component. Image analyzer 428 may also provide a reference image to interface devices 438, thereby allowing a user to define one or more subsets stored in parameters 436 which are used to compare the reference image to an inspection image.

Once a reference image has been defined, image analyzer 428 uses it to analyze inspection images from camera 104 taken of subsequent components. Image analyzer 428 detects component defects by determining if a variation exists between the reference image and the inspection image. For example, image analyzer 428 may perform image subtraction between the reference image and the inspection image or between a subset of the reference image and a subset of the inspection image, in order to detect a variation between the images.

If a variation is detection, image analyzer 428 may utilize one or more values in parameters 436 to determine if the component should be rejected. For example, a feature that is not precisely positioned on a component may still be acceptable within a certain distance, as defined by a threshold value in parameters 436. In such a case, controller 102 allows the component to be used (e.g., a rejection command is not generated). In other cases, no variation is allowed and all components that vary from that of the reference are rejected. If image analyzer 428 determines that the component in the inspection image is to be rejected, it then provides an indication of this to rejection command generator 430.

Rejection command generator 430 generates rejection commands that cause rejection device 424 to remove a rejected component from the manufacturing process. Rejection command generator 430 receives the indication from image analyzer 428 that the inspected component contains variations from that of the reference and generates a rejection command for rejection device 424. In some cases, the rejection command may be a direct command (e.g., controller 102 provides direct control over rejection device 424. In other cases, the rejection command may be indirect (e.g., another controller provides direct control over rejection device 424 to reject a component in response to receiving a rejection command). Additionally, the rejection command may cause an electronic signal to be generated or removed, in order to cause a component to be rejected. For example, rejection device 424 may only reject a component if an electronic signal is removed (e.g., is active-low). In such a case, the rejection command causes the signal to be removed, thereby rejecting the component.

Rejection command generator 430 may also maintain a history of rejection commands, in lieu of or in addition to, generating rejection commands. In some cases, controller 102 may provide the history to interface devices 438 and/or to other computing systems 440 for further analysis. In other cases, rejection command generator 430 may also utilize the history to determine if corrective measures should be taken. For example, if the number of rejections exceeds a threshold stored in parameters 436, this may indicate that corrective measures should be taken.

In some cases, rejection command generator 430 may determine that corrective action may be taken automatically and provide an indication of this to correction command generator 432. In response, correction command generator 432 generates a correction command that causes feature creating device 422 to change its operating state. For example, if feature creating device 422 is a printer having two or more heads, the correction command may be a switching command that causes the printer to switch heads. In this way, vision system 100 is able to automatically correct some sources of component defects without human interaction.

In other cases, rejection command generator 430 may determine that corrective action requires human interaction and generate one or more alerts 434. Alerts 434 are provided by controller 102 to interface devices 438 and/or to other computing systems 440 to alert a human operator that maintenance of feature creating device 422 may be necessary. In extreme cases, rejection command generator 430 may also generate a stop command that causes the manufacturing system to stop processing components until maintenance is performed.

Parameters 436 contain one or more values that affect how controller 102 functions. For example, parameters 436 may include an override value that, when set, disables the generation of rejection command by rejection command generator 430. In another example, parameters 436 may include one or more values that are used to determine when components are to be rejected, when alerts 434 are to be provided to a user via interface devices 438, and when correction commands should be generated. In some cases, parameters 436 may be pre-defined while, in other cases, parameters 436 may be provided by interface devices 438 and/or other computing systems 440.

Many modifications and variations are possible in light of the above description. The above-described descriptions of the various systems and methods may be used alone or in any combination thereof without departing from the scope of the invention. Although the description and figures may show a specific ordering of steps, it is to be understood that different orderings of the steps are also contemplated in the present disclosure. Likewise, one or more steps may be performed concurrently or partially concurrently. It is therefore intended to cover in the appended claims all such changes and modifications that are within the scope of this disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the systems and methods of this disclosure have been illustrated and described, it would be understood to those skilled in the art that various other changes and modifications can be made without departing from the spirit and scope of the invention. It is therefore intended to cover in the appended claims all such changes and modifications that are within the scope of this invention.

What is claimed is:

1. A method of inspecting a component of a hygienic article comprising:
storing, within a memory, a reference image of a first component used to produce a hygienic article, wherein the first component is free of defects and comprises a feature and wherein the reference image is captured when the first component passes a camera;
illuminating, at the camera, a second component with an illumination color that increases the contrast of a feature of the second component within an image, wherein the feature of the second component comprises a first color and a second color, wherein the first color has a corresponding first illumination color for increasing the contrast of the first color in an image and the second color has a corresponding second illumination color for increasing the contrast of the second color in an image, wherein the illumination color is an average of the first illumination color and the second illumination color;
triggering, by a trigger device, the capture of a single inspection image of the second component by the camera;
generating, by a processor, a residual image by performing image subtraction between the reference image and the inspection image;
detecting, by the processor, a variation between the first component and the second component using the residual image;
generating a rejection command that causes the second component to be rejected, in response to the variation being detected;
defining one or more boundaries in the reference image to indicate a subset of the reference image for comparison to the inspection image;
using the boundaries to select a subset of the inspection image that corresponds to the subset of the reference image;
determining, by the processor, if a plurality of rejection commands have been generated; and
issuing a switching command to a printer that causes the printer to switch between print heads of the printer, wherein the printer printed the graphic or text and
wherein the feature of the first component and the feature of the second component comprise a printed graphic or printed text; and
wherein the image subtraction is performed between the subset of the reference image and the subset of the inspection image.

2. The method of claim 1, further comprising illuminating the second component with a second illumination color that increases the contrast of a second feature of the second component.

3. The method of claim 1, wherein the reference image and the inspection image are in grayscale.

4. The method of claim 1, wherein the hygiene article is a feminine hygiene product.

5. The method of claim 1, wherein the hygiene article is an adult incontinence product.

6. The method of claim 1, wherein the hygiene article is a disposable diaper, a pull-on or a training pant.

7. A method of inspecting a component of a hygienic article comprising:
storing, within a memory, a reference image of a first component used to produce a hygienic article, wherein the first component is free of defects and comprises a feature and wherein the reference image is captured when the first component passes a camera;
illuminating, at the camera, a second component with a color that increases the contrast of a feature of the second component within an image , wherein the feature of the second component comprises a first color and a second color, wherein the first color has a corresponding first illumination color for increasing the contrast of the first color in an image and the second color has a corresponding second illumination color for increasing the contrast of the second color in an image, wherein the illumination color is an average of the first illumination color and the second illumination color;

triggering, by a trigger device, the capture of an inspection image of the second component by the camera;

generating, by a processor, a residual image by performing image subtraction between the reference image and the inspection image;

detecting, by the processor, a variation between the first component and the second component using the residual image;

generating a rejection command that causes the second component to be rejected, in response to the variation being detected;

determining, by the processor, if a plurality of rejection commands have been generated; and issuing a switching command to a printer that causes the printer to switch between print heads of the printer, wherein the printer printed the graphic or text;

wherein the feature of the first component and the feature of the second component comprise a printed graphic or printed text.

8. The method of claim 7, further comprising illuminating the second component with a second illumination color that increases the contrast of a second feature of the second component.

9. The method of claim 7, wherein the reference image and the inspection image are in grayscale.

10. The method of claim 7, further comprising:

defining one or more boundaries in the reference image to indicate a subset of the reference image for comparison to the inspection image;

using the boundaries to select a subset of the inspection image that corresponds to the subset of the reference image; and wherein the image subtraction is performed between the subset of the reference image and the subset of the inspection image.

11. A method of inspecting a component of a hygienic article comprising:

storing, within a memory, a reference image of a first component used to produce a hygienic article, wherein the first component is free of defects and comprises a feature and wherein the reference image is captured when the first component passes a camera;

illuminating, at the camera, a second component with a color that increases the contrast of a feature of the second component within an image, wherein the feature of the second component comprises a first color and a second color, wherein the first color has a corresponding first illumination color for increasing the contrast of the first color in an image and the second color has a corresponding second illumination color for increasing the contrast of the second color in an image, wherein the illumination color is an average of the first illumination color and the second illumination color;

triggering, by a trigger device, the capture of a single inspection image of the second component by the camera;

defining one or more boundaries in the reference image to indicate a subset of the reference image for comparison to the inspection image;

using the boundaries to select a subset of the inspection image that corresponds to the subset of the reference image;

generating, by a processor, a residual image by performing image subtraction between the subset of the reference image and the subset of the inspection image;

detecting, by the processor, a variation between the first component and the second component using the residual image; and generating a rejection command that causes the second component to be rejected, in response to the variation being detected.

12. The method of claim 11, wherein the feature of the first component and the feature of the second component comprise a printed graphic or printed text.

13. The method of claim 12, further comprising:

determining, by the processor, if a plurality of rejection commands have been generated; and issuing a switching command to a printer that causes the printer to switch between print heads of the printer, wherein the printer printed the graphic or text.

14. The method of claim 11, further comprising illuminating the second component with a second illumination color that increases the contrast of a second feature of the second component.

15. The method of claim 11, wherein the second component has two or more features that differ in color and the second component is illuminated with a color that is an average of colors that increase the contrast of the two or more features.

16. The method of claim 11, wherein the reference image and the inspection image are in grayscale.

* * * * *